United States Patent [19]

Ichikawa et al.

[11] 4,100,180

[45] Jul. 11, 1978

[54] PROCESS FOR HYDROGENATING UNSATURATED ALDEHYDES TO UNSATURATED ALCOHOLS

[75] Inventors: Yataro Ichikawa; Nobuo Suzuki; Toru Sawaki, all of Iwakuni, Japan

[73] Assignee: Teijin, Limited, Osaka, Japan

[21] Appl. No.: 643,953

[22] Filed: Dec. 23, 1975

[30] Foreign Application Priority Data

Dec. 26, 1974 [JP] Japan .................................. 49-148267
Dec. 26, 1974 [JP] Japan .................................. 49-148268

[51] Int. Cl.² ...................... C07C 29/14; C07D 307/42
[52] U.S. Cl. ................................. 260/347.8; 568/881; 568/813; 568/875; 568/824
[58] Field of Search ............ 260/347.8, 617 C, 618 H, 260/631.5, 638 B

[56] References Cited

FOREIGN PATENT DOCUMENTS 1,158,960   12/1963   Fed. Rep. of Germany.

OTHER PUBLICATIONS

Organic Synthesis (Gilman et al.), Collective vol. I, (1948) pp. 463-470.
Adams et al., J. Am. Chem. Soc., vol. 48, pp. 477-482, (1926).
Tuley et al., J. Am. Chem. Soc., vol. 47, pp. 3061-3068, (1925).

Primary Examiner—Natalie Trousof
Assistant Examiner—Bernard Dentz
Attorney, Agent, or Firm—Wenderoth, Lind & Ponack

[57] ABSTRACT

A solid catalyst for preparation of unsaturated alcohols by selective hydrogenation of the aldehyde group of unsaturated aldehydes, said catalyst comprising platinum oxide and deposited on its surface in an atmosphere of hydrogen, an iron compound and a zinc compound, and an improved process for preparing unsaturated alcohols by catalytic hydrogenation of unsaturated aldehydes with hydrogen in the presence of the aforesaid catalyst.

5 Claims, No Drawings

PROCESS FOR HYDROGENATING UNSATURATED ALDEHYDES TO UNSATURATED ALCOHOLS

This invention relates to a novel catalyst composition, and more specifically, to a solid catalyst composed of platinum oxide and deposited on its surface in an atmosphere of hydrogen, an iron compound and a zinc compound, and a process for preparing unsaturated alcohols by selectively hydrogenating the aldehyde group of unsaturated aldehydes using this solid catalyst.

In the hydrogenation of unsaturated aldehydes, unsaturated bonds are generally more susceptible to hydrogenation than aldehyde groups, and in order to hydrogenate the aldehyde group of an unsaturated aldehyde selectively to form the corresponding unsaturated alcohol, special hydrogenating conditions are required.

One of the prior techniques for selectively hydrogenating the aldehyde group of an unsaturated aldehyde to the corresponding unsaturated alcohol comprises hydrogenating unsaturated aldehydes in the presence of platinum oxide as a hydrogenating catalyst and in the copresence of an iron salt and/or a zinc salt thereby to form the corresponding unsaturated alcohol [see, for example, R. Adams and B. S. Garvey, J. Am. Chem. Soc., 48, 477 (1926); and P. N. Rylander, N. Himelstein and N. Kilroy, Engelhard Ind. Tech. Bull., 4, 49 (1963)].

With the above prior technique, however, it is difficult to separate the catalyst from the reaction mixture, and long periods of time are required for the separation. Even after the separating procedure, the solid catalyst still remains in a colloidal form in the reaction product and is difficult to remove by ordinary separating methods. The reaction product also contains large quantities of the platinum catalyst, the iron compound and zinc compounds dissolved therein. Thus, when the reaction product as such is distilled, the resulting unsaturated alcohol and/or unreacted unsaturated aldehyde causes undesirable side reactions, and the rate of recovery of the desired alcohol and the unreacted aldehyde is markedly reduced. In addition, when the unsaturated alcohol is prepared continuously by repeatedly using the above catalyst, the selectivity of the unsaturated alcohol decreases within very short periods of time, and this naturally causes a marked decline in the yield of the unsaturated alcohol. The above conventional techniques are therefore unsatisfactory.

It is an object of this invention to provide a novel catalyst comprising platinum oxide, an iron compound and a zinc compound which is free from the abovementioned defects.

Another object of this invention is to provide a solid catalyst for the hydrogenation of unsaturated aldehydes, which is very easy to separate from the reaction product, ensures a very high selectivity of unsaturated alcohols, and maintains the selectivity of unsaturated alcohols over long periods of time even when used continuously and repeatedly.

Still another object of this invention is to provide a process for preparing unsaturated alcohols, which comprises hydrogenating the aldehyde group of an unsaturated aldehyde using the above-mentioned novel catalyst.

Other objects and advantages of this invention will become apparent from the following detailed description of the invention.

According to the present invention, there is provided a solid catalyst for converting an unsaturated aldehyde to an unsaturated alcohol by selective hydrogenation of its aldehyde group, said catalyst comprising platinum oxide and deposited on its surface in an atmosphere of hydrogen, an iron compound and a zinc compound.

The essential difference of the solid catalyst of this invention from the conventional catalyst is that in the catalyst of this invention, the iron compound and zinc compound are deposited in an atmosphere of hydrogen on the surface of platinum oxide.

The solid catalyst of this invention, based on platinum oxide which is prepared in an atmosphere of hydrogen, has the iron compound and zinc compound adhered firmly to the surface of the platinum oxide base, and the iron compound and zinc compound dissolve in the reaction mixture only in negligible amounts. Furthermore, since the catalyst readily agglomerates to form stable particles having a suitable amount, the solid catalyst can be simply separated and recovered from the reaction product within extremely short periods of time after the reaction, and losses are small. In addition to those very superior commercial advantages, the solid catalyst of this invention is characterized by being prepared in advance before a hydrogenation reaction of unsaturated aldehydes, and when used to prepared unsaturated alcohols by this reaction, ensures a very high selectivity of unsaturated alcohols as compared with the conventional platinum oxide-based solid catalysts. This high selectivity can be maintained over a long period of time even when the catalyst is used repeatedly.

The solid catalyst of this invention conveniently has a surface area of 10 to 60 $m^2/g$, preferably 12 to 50 $m^2/g$. In the present specification and the appended claims, the "surface area" of the catalyst is measured by the BET method usually employed for measuring the surface areas of solid catalysts. Specifically, the surface area is measured by means of "Sorptometer 21D Type" supplied by Perkin-Elmer Company, and expressed in square meter per gram of solid catalyst ($m^2/g$).

All grades of platinum oxide which are usually employed as hydrogenating catalysts can be used as a basic ingredient of the solid catalyst of this invention. For example, those generically called Adams-type platinum oxide can be suitably used [see "Organic Synthesis", Col. Vol. 1, 463 (1948)]. The particle diameter of the solid catalyst of this invention is not particularly limited, but is preferably about 1 to 3 microns.

The iron compound and zinc compound to be deposited onto the surface of the platinum oxide may be of any kind, but are preferably those which are at least partly soluble in inert organic solvents to be used for catalyst preparation as will be described below. Examples of suitable metal compounds are inorganic acid salts of iron or zinc such as sulfates, nitrates, phosphates, halides (e.g. chlorides), and carbonates; and organic acid salts of iron or zinc, especially lower ($C_1$–$C_4$) aliphatic mono-or di-carboxylic acid salts such as acetates, formates and oxalates. Of these, iron and zinc sulfates or acetates are especially advantageous.

The valency of iron in the iron compound is not critical, but it may be either mono-, di-, tri-, tetra-or penta-valent. Preferably, it is di- or tri-valent, above all, divalent. Thus, ferrous sulfate and ferrous acetate are preferred as the iron compound.

On the other hand, zinc in the zinc compound is present usually as a divalent metal, and zinc sulfate and zinc acetate are preferred as the zinc compound.

The amounts of the iron compound and the zinc compound deposited to the surface of platinum oxide are such that the amounts of these compounds present in the skin layer extending from the surface of the solid catalyst into a depth of 1 micron toward its inside are preferably 1.5 to 70% by weight, more preferably 1.5 to 50% by weight, calculated as iron, and preferably 0.5 to 8% by weight, more preferably 2.5 to 7% by weight, calculated as zinc, respectively based on the total amount of the platinum oxide, iron compound and zinc compound present in the skin layer. Therefore, the amount of the platinum oxide in the skin layer can be 98.0 to 22% by weight, preferably 96 to 43% by weight, calculated as platinum.

In the present specification and the appended claims, the amounts of the iron compound and the zinc compound deposited are determined by the following method.

Using an X-Ray Analyzer (an electron microprobe X-ray analyzer, Model 2A, a product of Shimazu-ARL Company), the amounts of platinum oxide, the iron compound and the zinc compound present in a skin layer of a sample solid catalyst which extends from its surface to a depth of 1 micron toward its inside are measured under the following conditions.

Accelerating voltage: 30 KV
Sample current: 0.0013 $\mu$A
Take off angle of X-rays from sampe surface: 52.5°
Dispersible crystal: LiF
Detector: Kr-Exatron
X-ray diameter: 2$\mu$m
Sample speed: 96 $\mu$m/min.
X-rays used:
Fe $K_\alpha$ 1.937 A
Zn $K_\alpha$ 1.436 A
Pt $L_\alpha$ 1.313 A Based on the amounts of the platinum oxide, iron compound and zinc compound measured by the above method, the iron retention and the zinc retention were determined in accordance with the following definitions.

$$\text{Iron retention } (X) = \frac{\left(\begin{array}{l}\text{Weight of the iron compound}\\ \text{calculated as metal}\end{array}\right)}{\left(\begin{array}{l}\text{Total weight of the platinum oxide, iron compound}\\ \text{and zinc compound calculated as metals}\end{array}\right)} \times 100$$

$$\text{Zinc retention } (Y) = \frac{\left(\begin{array}{l}\text{Weight of the zinc compound}\\ \text{calculated as metal}\end{array}\right)}{\left(\begin{array}{l}\text{Total weight of the platinum oxide, iron compound}\\ \text{and zinc compound calculated as metals}\end{array}\right)} \times 100$$

The solid catalyst of this invention can be prepared, for example, by bringing platinum oxide into contact with the iron compound and zinc compound simultaneously or in an optional order in an inert solvent in an atmosphere of hydrogen prior to use in the hydrogenation of unsaturated aldehydes.

Any inert organic solvent which is stable in an atmosphere of hydrogen can be used in this invention. However, for practical purposes, the same solvent as used in the hydrogenation reaction of unsaturated aldehydes using the solid catalyst of this invention may be employed. Usually, lower ($C_1$-$C_4$) aliphatic alcohols such as methanol or ethanol are suitable.

It is important and critical in the preparation of the catalyst of this invention that the contacting of platinum oxide with the iron compound and zinc compound is performed in an atmosphere of hydrogen.

We found that a solid catalyst prepared by treating platinum oxide in an atmosphere of hydrogen until the absorption of hydrogen stops and depositing an iron compound and a zinc compound on the treated platinum oxide does not have superior advantages even if the deposition is performed in an atmosphere of hydrogen. However, a solid catalyst prepared by contacting untreated platinum oxide with an iron compound had a zinc compound in an atmosphere of hydrogen exhibits the various advantages described above.

Thus, the catalyst is prepared in accordance with this invention in an atmosphere of hydrogen having a partial pressure of generally 0.1 to 300 Kg/cm$^2$, preferably 0.2 to 200 Kg/cm$^2$. Hydrogen may be present in a pure form, or as a mixture with an inert gas such as nitrogen, carbon dioxide, helium or argon.

The temperature used at the time of catalyst preparation is not critical, but can be chosen from a wide range of temperatures. The temperature is generally $-40°$ to 200° C., preferably $-10°$ to 150° C., most usually room temperature. The reaction time differs according, for example, to the types or amounts of the iron compound and zinc compound, or the reaction temperature. Usually periods of 1 minute to 10 hours are sufficient.

One example of catalyst preparation comprises suspending platinum oxide in an inert organic solvent, adding an iron compound and a zinc compound to the suspension either simultaneously or in this order or in a reverse order, and contacting them with each other in an atmosphere of hydrogen. When the iron compound and zinc compound are added sequentially, there can, for example, be employed a procedure which comprises first adding the iron compound to the suspension and contacting it fully with the platinum oxide in an atmosphere of hydrogen, and then adding the zinc compound and contacting it fully with the platinum oxide so-treated in the hydrogen atmosphere.

In the catalyst preparation, the iron compound and the zinc compound can be added in amounts of 0.04 to 0.8 parts by weight, preferably 0.04 to 0.5 part by weight, per part by weight of platinum oxide, calculated as metallic iron, and 0.01 to 0.3 part by weight, preferably 0.01 to 0.2 part by weight, per part by weight of platinum oxide, calculated as metallic zinc, respectively.

In the resulting solid catalyst, the iron compound and the zinc compound adhere firmly to the platinum oxide base, and usually, the catalyst has an average particle diameter of 10 to 100 microns. It can be present in the form of an agglomerate having very superior settling properties in the reaction mixture.

The solid catalyst so-prepared can be isolated by conventional separating procedures such as settling separation, centrifugal separation or filtration. The catalyst separated may, if desired, be washed with a suitable solvent such as the one used in the catalyst preparation, or the solvent as used in the hydrogenation reaction using the resulting catalyst. It may be also used with or without prior drying.

The catalyst of this invention can be used for selectively hydrogenating the aldehyde group of an unsaturated aldehyde to prepare the corresponding unsaturated alcohol.

Thus, according to this invention, there is provided an improved process for preparing unsaturated alcohols by catalytically hydrogenating unsaturated aldehydes with hydrogen in the presence of the new solid catalyst of this invention described above.

The unsaturated aldehyde that can be hydrogenated with the catalyst of this invention is an organic compound containing at least one unsaturated bond and at least one aldehyde group (CHO) in the molecule, and may include any of aliphatic, aromatic, alicyclic and heterocyclic unsaturated aldehydes. These unsaturated aldehydes may contain in the molecule an inert atom or group which does not participate in the hydrogenation reaction, such as hydroxyl group, an amino group or a halogen atom.

The catalyst of this invention is very suitable for selectively hydrogenating an aldehyde group (CHO) to a hydroxymethyl group (CH$_2$OH). Even when the starting material is an unsaturated aldehyde containing an easily reducible α,β-unsaturated bond in the molecule, the hydrogenating catalyst of this invention can reduce the aldehyde group selectively to afford the corresponding unsaturated alcohol in high selectivities and high conversions.

Accordingly, the catalyst of this invention is a very suitable catalyst for hydrogenating α,β-unsaturated aldehydes, especially those of the following formula

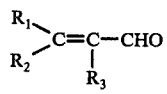 (I)

wherein R$_1$ is a saturated or unsaturated hydrocarbon group, and R$_2$ and R$_3$, identical or different to or from each other, represent a hydrogen atom, a saturated or unsaturated hydrocarbon group or a heterocyclic group, to form the corresponding α,β-unsaturated alcohols of the following formula

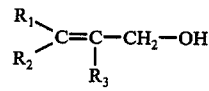 (II)

Preferred species of the α,β-unsaturated aldehyde are those of formula (I) wherein R$_1$, R$_2$ and R$_3$ contain not more than 50, preferably not more than 30, carbon atoms and each represents an alkyl group, an alkenyl group, an alkynyl group, an alicyclic group, an aromatic group, a heterocyclic group containing an oxygen, sulfur or nitrogen atom, a group formed by bonding at least two of these groups, or a heterocyclic group formed by bonding at least two of these groups through an oxygen, sulfur or nitrogen atom. Those in which R$_1$, R$_2$ and R$_3$ contain not more than 50, preferably not more than 30, carbon atoms and each represents a group selected from alkyl, alkenyl, alicyclic and aromatic groups are especially preferred. In this case, one or both of R$_2$ and R$_3$ may be a hydrogen atom, and R$_1$, R$_2$ and R$_3$ may be substituted by a substituent such as an alkoxy group containing not more than 5 carbon atoms (e.g., methoxy, ethoxy, n-propoxy, iso-propoxy, butoxy or pentoxy), an alkoxycarbonyl group containing not more than 6 carbon atoms (e.g., methoxycarbonyl, ethoxycarbonyl, n-propoxycarbonyl, butoxycarbonyl or pentoxycarbonyl), and a halogen atom (e.g., fluorine, chlorine or bromine). Each of R$_1$, R$_2$ and R$_3$ may be substituted by 1 to 3 of these substituents.

In particular, it is preferable to use α,β-unsaturated aldehydes of formula (I) in which R$_1$ is an alkyl group containing 1 to 30 carbon atoms or an alkenyl group containing 2 to 30 carbon atoms, and R$_2$ and R$_3$ represent a hydrogen atom or an alkyl group containing 1 to 5 carbon atoms.

Specific examples of the α,β-unsaturated aldehydes that can be used in this invention are given below. It should be noted, however, that the invention is in no way limited to these exemplified species.

(1) Aliphatic aldehydes
3-Ethyl-buten-2-al-1, 3-propylbuten-2-al, 3-butylbuten-2-al-1, 3,3-ethylpropyl-acrolein, 2-ethylhexen-2-al-1, 2-ethylisohexen-2-al-1, 2,6-nonadienal, 2-n-amyl-crotonaldehyde, 2-hexyl-crotonaldehyde, 2-propylideneenaathaldehyde, 2-octylcrotonaldehyde, citral, diisovaleraldehyde, dihydrocitral, 6-methylcitral, citrylideneacetaldehyde, citrylidenepropyonaldehyde, farnesal, and geranyl geranial.

(2) Alicyclic aldehydes
Cyclocitrylideneacetaldehyde, cyclocitrylidenepropionaldehyde, methylional, ionylideneacetaldehyde, Vitamine A aldehyde, dihydroretinal, and tetrahydroretinal.

(3) Aromatic aldehydes
Cinnamaldehyde, nuciferal, 2-ethylcinnamaldehyde, 2-isopropylcinnamaldehyde, 2-n-butylcinnamaldehyde, 2-hexylcinnamaldehyde, p-methylcinnamaldehyde, 2-methyl-2-isopropylphenyl acrolein, 5-phenyl-2-pentene-1-al and benzylidene citronellal.

(4) Heterocyclic aldehydes
2-Methyl-3-furyl-acrolein, 2-ethyl-3-furylacrolein, 2-propyl-furyl-acrolein, 3-methyl-4-furylidenebutyraldehyde, and 5-(2-furyl)-3-methyl-2-pentenal.

Of these, the aldehydes exemplified in (1) and (2), especially the aliphatic α,β-unsaturated aldehydes mentioned in (1), are most preferred.

The hydrogenation of the unsaturated aldehyde can be carried out by per se known methods. Advantageously, the hydrogenation reaction in this invention is carried out, for example, at −40° to 300° C., preferably 10° to 200° C. The suitable partial pressure of hydrogen is 0.5 to 300 Kg/cm$^2$, preferably 0.8 to 200 Kg/cm$^2$.

Hydrogen used for hydrogenation may be pure hydrogen or a mixture of hydrogen with an inert gas such as nitrogen, carbon dioxide or argon.

The hydrogen can be contacted with the unsaturated aldehyde countercurrently or concurrently.

The hydrogenation reaction in this invention does not particularly require the use of solvent. If desired, however, it can be carried out in a solvent. The solvent is preferably one which can substantially dissolve the unsaturated aldehyde as a starting material. Lower (C$_1$–C$_4$) aliphatic alcohols such as methanol or ethanol are especially preferred species.

Desirably, the hydrogenation reaction is carried out in the presence of water. By using water in an amount of not more than 20 molar times, especially 0.6 to 5 molar times, the starting unsaturated aldehyde, the selectivity of the corresponding unsaturated alcohol can be increased.

The hydrogenation reaction can be carried out either batchwise or continuously. In any of these methods, the same solid catalyst can be used repeatedly by recycling. In recycling the used catalyst, a fresh supply of the solid catalyst may be added.

The active lifetime of the solid catalyst can be maintained even longer by adding 0.0002 to 0.03 part by weight, preferably 0.0002 to 0.004 part by weight, and 0.0002 to 0.004 part by weight, preferably 0.0002 to 0.0025 part by weight, calculated as metallic iron and metallic zinc respectively per part by weight of platinum oxide in the solid catalyst to the solid catalyst to be recycled. It has been found that for example, even after using the solid catalyst 30 times, this additional supply of the iron and zinc compounds makes is possible to maintain high selectivity and conversion in hydrogenating unsaturated aldehyde to unsaturated alcohols.

The iron compound and the zinc compound may be added to the solid catalyst separated from the reaction mixture, or to the solid catalyst recycled to the reaction system.

The hydrogenation reaction in accordance with this invention can be preformed by use of the suspending method, fixed bed method, fluidized bed method or moving bed method.

The present invention can produce unsaturated alcohols in high yields resulting from the conversion of the aldehyde group (CHO) of the starting unsaturated aldehydes to a hydroxymethyl group ($CH_2OH$). For example, geraniol and prenol can be prepared in high yields from citral and β-methylcrotonaldehyde.

The desired unsaturated alcohol can be separated and recovered from the reaction mixture by customary methods.

For example, after the reaction, the hydrogenation reaction mixture is subjected to a procedure of separating the solid catalyst from it by known methods either at the reaction temperature or after being cooled.

Any conventional separating methods can be used for this purpose. For example, there can be used a method in which after the reaction, the reaction product, either as contained in the reactor, or after being transferred to another vessel, is allowed to stand to sediment the solid catalyst, and the upper phase is extracted. Or the solid catalyst can be separated by filtration or centrifugal separation.

The solid catalyst of this invention has good settling properties as mentioned above, and by the above separating procedures, it can be separated almost completely. Sometimes, fine particles of the solid catalyst are still present in the reaction mixture after the above separating procedure. In such a case, the above separating procedure is repeated to completely separate the solid catalyst.

The reaction product from which the solid catalyst has been separated can be directly subjected to a purifying procedure such as distillation. Sometimes, the reaction mixture contains the iron compound and/or zinc compound dissolved out from the solid catalyst, and/or the solid catalyst remaining unseparated. When the iron compound, the zinc compound and the solid catalyst are present in an amount of more than 100 ppm, more than 100 ppm, and more than 10 ppm calculated as metallic iron, metallic zinc and metallic platinum, respectively, based on the total amount of the unsaturated alcohol and the unreacted unsaturated aldehyde in the reaction product. The reaction mixture is advantageously purified, for example, by distilling it after removing the above components until their amounts in the reaction mixture become less than 60 ppm, less than 60 ppm, and less than 5 ppm respectively by such means as adsorption or extraction.

The distillation can be performed by a per se known method. The temperature at which distillation is carried out varies according to the types of the unsaturated alcohol and the unreacted unsaturated aldehyde. But since the alcohol and aldehyde generally have poor stability, the distillation is carried out usually at 10° to 300° C., preferably 50° to 200° C. The pressure may be normal atmospheric pressure or reduced pressure. Frequently, the distillation is carried out at a reduced pressure.

For example, the reaction product containing prenol obtained by the hydrogenation of β-methylcrotonaldehyde is distilled at a temperature of 20° to 140° C. and a pressure of 1 to 760 mmHg, especially at a temperature of 30° to 100° C. and a pressure of 1 to 180 mmHg. The product containing geraniol obtained by the hydrogenation of citral is distilled at a temperature of 50° to 200° C. and a pressure of 0.3 to 300 mmHg, especially a temperature of 70° to 180° C. and a pressure of 1 to 180 mmHg.

Any conventional distillation devices, such as the tray type, packed type or thin film distillation type, can be used for the above distillation operation.

Thus, according to this invention, the intended unsaturated alcohol can be obtained in a high yield.

The present invention makes it possible to achieve high selectivity and high conversion of unsaturated aldehydes to unsaturated alcohols, and since the reaction mixture to be distilled has a low content of unreacted unsaturated aldehyde which will react with the resulting unsaturated alcohol to reduce the rate of recovery of the alcohol, the unsaturated alcohol of high purity can be obtained at a high rate of recovery.

The distillation can be carried out either batchwise or continuously, and preferably, in an atmosphere of an inert gas such as nitrogen, argon or helium. In the performance of the distillation, known stabilizers such as amine compounds, hydroquinones or weak acids can be added in order to prevent the degeneration of the unsaturated aldehydes.

Although the above description has been directed to a preferred embodiment in which the separation and purification of the unsaturated alcohol is effected by distillation, this is in no way limitative. Other separating and purifying methods such as chromatography or recrystallization can, of course, be employed in this invention.

The following Examples illustrate the present invention more specifically.

EXAMPLE 1-A

A 500 cc autoclave equipped with an electromagnetically rotating stirrer was charged with 0.5 part of platinum oxide, 150 parts of 90% methanol, 0.375 part of ferrous sulfate heptahydrate and 0.0825 part of zinc acetate dihydrate. The inside of the autoclave was fully purged first with nitrogen and then with hydrogen, and then hydrogen was introduced to a partial pressure of 10 Kg/cm².G. The mixture was stirred at room temperature for 2 hours. Then, the stirring was stopped, and the platinum oxide was separated by sedimentation. In 10 minutes, the platinum oxide settled. The sedimentation was repeated two more times using 100 parts of 90% methanol each time to afford a catalyst.

Analysis of a small amount of the sample catalyst so prepared showed that it has a surface area of 15.0 m²/g, an iron retention of 2.4% by weight and a zinc retention of 5.6% by weight.

The same 500 cc autoclave was charged with 0.4 part of the catalyst so prepared, 21 parts of β-methylcrotonaldehyde, 150 parts of 90% methanol, 0.0037 part of ferrous sulfate heptahydrate, and 0.0024 part of zinc acetate dihydrate. The inside of the autoclave was fully purged first with nitrogen and then with hydrogen, and hydrogen was introduced into it to a partial pressure of 30 Kg/cm$^2$.G. At this pressure, the mixture was stirred and reacted for 6 hours. Then, the stirring was stopped, and the autoclave was purged with nitrogen, after which the reaction mixture was allowed to stand for 15 minutes.

The supernatant liquid was gently taken out to obtain 171 parts of the reaction mixture. Then, while leaving the catalyst in the autoclave, β-methylcrotonaldehyde, 90% methanol, ferrous sulfate heptahydrate and zinc acetate dihydrate were again fed into the autoclave in the same proportions as described above, and the same reaction as above was carried out. The reaction mixture was transparent and colorless, and contained less than 1 ppm, 20 to 25 ppm, and 20 to 22 ppm, as metals, of platinum, iron and zinc based on the total weight of the β-methylcrotonaldehyde and prenol in the reaction mixture. The results are shown in Table 1.

A part of the catalyst remaining in the autoclave was taken out, and its particle diameter was measured. It was found to have an average particle diameter of 25 microns which was considerably larger than that of platinum oxide before catalyst preparation (2 microns).

The reaction mixture was fed into a flask equipped with a packed rectification tower, and methanol was removed at 200 mmHg. abs. Then, the reaction was raised to 50 mmHg. abs., and distillation of prenol was performed. The rate of recovery of prenol by distillation was 95%, and the rate of recovery of the unreacted β-methylcrotonaldehyde by distillation was 94%. The rate of recovery of each component by distillation is defined by the following equation.

$$\text{Rate of recovery of each component} = \frac{\begin{bmatrix}\text{(Amount of each component in the distillate)} + \\ \text{(amount of each component in the flask residue)}\end{bmatrix} \times 100}{\text{Amount of each component in the feed raw material}}$$

Table 1

| Number of reaction cycles | Conversion (%) | Selectivity to (%) | | |
|---|---|---|---|---|
| | | Prenol | Isoamyl alcohol | Isovaleroaldehyde |
| 1 | 75 | 95.0 | 3.5 | 1.5 |
| 10 | 76 | 94.8 | 3.6 | 1.6 |
| 20 | 74 | 95.5 | 3.4 | 1.1 |
| 30 | 73 | 94.2 | 3.7 | 1.1 |

EXAMPLE 1-B

The same autoclave as used in Example 1-A was charged with 0.5 part of a catalyst prepared in the same way as in Example 1-A, 21 parts of β-methylcrotonaldehyde, and 150 parts of 90% methanol, and the catalyst was used through 8 cycles in the same way as in Example 1-A except that ferrous sulfate heptahydrate and zinc acetate dihydrate were not used. The resulting reaction mixture was colorless and transparent in all runs, and contained less than 1 ppm, 33 ppm, and 26.6 ppm as metals of platinum, iron and zinc respectively based on the total amount of β-methylcrotonaldehyde and prenol in the reaction mixture. In the first run, the conversion of β-methylcrotonaldehyde was 74%, and the selectivity to prenol was 95.0%. In the sixth run, the conversion of β-methylcrotonaldehyde was 76%, and the selectivity to prenol was 91.0%. In the eighth run, no change in conversion was observed, but the selectivity to prenol fell to 88.0%.

EXAMPLE 2

A 500 cc autoclave equipped with an electromagnetically rotating stirrer was charged with 0.5 part of platinum oxide, 150 parts of 90% methanol, 0.375 part of ferrous sulfate heptahydrate and 0.0825 part of zinc acetate dihydrate, and a catalyst was prepared in the same way as in Example 1-A. Analysis of a small amount of the sample catalyst showed that it had a surface area of 14.6 m$^2$/g, an iron retention of 2.6% by weight and a zinc retention of 5.6% by weight.

The autoclave was charged with the resulting catalyst, 38 parts of citral, 150 parts of 90% methanol, 0.0037 part of ferrous sulfate heptahydrate and 0.0024 part of zinc acetate dihydrate. The inside of the autoclave was purged fully with nitrogen and then with hydrogen, and hydrogen was introduced into it to a partial pressure of 30 Kg/cm$^2$.G. At this pressure, the mixture was stirred, and the reaction was performed for 6 hours. Then, the stirring was stopped, and the inside of the autoclave was purged with nitrogen, after which the contents of the autoclave were allowed to stand for 15 minutes. The supernatant liquid was gently taken out to afford 188 parts of the reaction mixture. While leaving the catalyst in the autoclave, citral, 90% methanol, ferrous sulfate heptahydrate, and zinc acetate dihydrate were fed into the autoclave in the same proportions as described above, and the reaction was repeatedly carried out.

In all runs, the reaction mixture was colorless and transparent, and contained less than 1 ppm, 15 to 25 ppm, and 7 to 25 ppm as metals of platinum, iron and zinc based on the total amount of citral and geraniol and nerol. The results are shown in Table 2.

The catalyst remaining in the autoclave had an average particle diameter of 20 microns which was considerably larger than that of platinum oxide before catalyst preparation (2 microns).

A flask equipped with a rotary band rectification column was charged with the reaction mixture, and methanol was removed at 200 mmHg. abs. Then, distillation of geraniol was performed at 5 mmHg. abs. As a result, the rate of recovery of geraniol by distillation was 94%, and the rate of recovery of the unreacted citral was 93%. The rates of recovery of these components were as defined in Example 1-A.

Table 2

| Number of reaction cycles | Conversion (%) | Selectively to (%) | | |
|---|---|---|---|---|
| | | Geraniol Nerol | Citronellol | Others |
| 1 | 70 | 94.5 | 3.2 | 2.3 |
| 10 | 72 | 93.0 | 3.1 | 3.9 |
| 20 | 69 | 94.0 | 3.3 | 2.7 |
| 30 | 71 | 95.1 | 3.0 | 1.9 |

COMPARATIVE EXAMPLE 1

The same 500 cc autoclave as used in Example 1 was charged with 0.5 part of platinum oxide, 38.0 parts of citral, 150 parts of 90% methanol, 0.375 part of ferrous sulfate heptahydrate and 0.0825 part of zinc acetate dihydrate. The inside of the autoclave was fully purged with nitrogen and then with hydrogen, after which hydrogen was introduced into the autoclave to a partial pressure of 30 Kg/cm$^2$.G. At this pressure, the mixture was stirred for 4 hours, and then the stirring was stopped, after which the inside of the autoclave was purged with nitrogen, and its contents were allowed to stand for one day. The supernatant liquid was gently taken out to separate the catalyst from 188 parts of the reaction mixture. Analysis of a small amount of the sample catalyst so separated showed that it had a surfce area of 6.8 m$^2$/g, an iron retention of 5.2%, and zinc retention of 5.7%. It is seen that the surface area was reduced as compared with the catalyst prepared in Example 2.

The reaction mixture was black and almost void of transparency, and contained 140 ppm, 1680 ppm, and 175 ppm as metals of platinum, iron and zinc respectively based on the total amount of citral, geraniol, nerol and citronellol. In the first run, the conversion of citral was 72%, and the selectivity to the corresponding unsaturated alcohol (geraniol and nerol) was 89%.

The catalyst remaining in the autoclave had an average particle diameter of 2 microns which was the same as that of platinum oxide before catalyst preparation.

The reaction mixture was fed into a flask equipped with a rotary band rectification column, and methanol was removed at 200 mmHg. abs., and then distillation of geraniol was carried out at 5 mmHg. abs. The rate of recovery of geraniol by distillation was 67%, and the rate of recovery of the unreacted citral by distillation was 120%. The amount of citral recovered increased over that initially charged. The rates of recovery of these components by distillation were the same as defined in Example 1-A.

Comparative Example 2

The same 500 cc autoclave as used in Example 1-A was charged with 0.5 part of platinum oxide and 150 parts of 90% methanol, and the inside of the autoclave was charged fully with nitrogen and then with hydrogen. Then, hydrogen was introduced into the autoclave to a pressure of 10 Kg/cm$^2$.G. The mixture was stirred at this pressure for 2 hours. Then, the stirring was stopped, and platinum oxide was sedimented and separated. In 30 minutes, the platinum oxide was settled. This sedimentation procedure was repeated two more times using 100 parts of 90% methanol each time to afford a catalyst. Analysis of a small amount of the catalyst prepared showed that it had a surface area of 30 m$^2$/g, an iron retention of 0.4% and a zinc retention of 0%. The presence of a trace of iron on the catalyst was considered as due to the presence of iron in 90% methanol used.

The autoclave was charged with the treated platinum oxide, 21 parts of β-methylcrotonaldehyde and 150 parts of 90% methanol. The inside of the autoclave was fully purged first with nitrogen and then with hydrogen, and hydrogen was introduced into the autoclave to a partial pressure of 30 Kg/cm$^2$.G. The mixture was stirred for 6 hours at this pressure, and then allowed to stand for 30 minutes to separate the catalyst by sedimentation. 171 parts of the reaction mixture was obtained.

The conversion of β-methylcrotonaldehyde was 60.6%, and the selectivity to prenol was 3.8%. Isovaleroaldehyde and isoamyl alcohol also occurred.

Comparative Example 3

The same 500 cc autoclave as used in Example 1-A was charged with 0.5 part of platinum oxide and 150 parts of 90% methanol. The inside of the autoclave was fully purged first with nitrogen and then with hydrogen, and hydrogen was introduced into the autoclave to a partial pressure of 10 Kg/cm$^2$.G. The mixture was stirred at this pressure for 1 hour, and then the stirring was stopped, after which the contents of the autoclave were allowed to stand for 30 minutes to sediment and separate platinum oxide. The supernatant liquid was extracted gently, and then 0.375 part of ferrous sulfate heptaldehyde 0.0825 part of zinc acetate dihydrate and 150 parts of 90% methanol were added. The inside of the autoclave was again purged with nitrogen and hydrogen. Hydrogen was introduced into the autoclave to a partial pressure of 10 Kg/cm$^2$.G. The mixture was stirred for 1 hour at this temperature, and then the stirring was stopped. The contents of the autoclave were allowed to stand for 30 minutes to sediment and separate platinum oxide. This sedimentation procedure was repeated two more times using 100 parts of 90% methanol each time to prepare a catalyst. Analysis of a small amount of the catalyst prepared showed that it had a surface area of 14.6 m$^2$/g, an iron retention of 0.7% by weight and a zinc retention of 3% by weight.

The resulting platinum oxide catalyst, 38 parts of citral and 150 parts of 90% methanol were fed into the autoclave, and then, the inside of the autoclave was fully purged with nitrogen and then with hydrogen. Hydrogen was then introduced into the autoclave to a partial pressure of 30 Kg/cm$^2$.G, and the mixture was stirred at this pressure for 6 hours, after which the contents of the autoclave were allowed to stand to sediment and separate the catalyst. 188 parts of the reaction mixture was obtained.

The conversion of citral was 23.8%, and the selectivity to geraniol and nerol was 54.2%. Citronellol, 2,6-dimethyloctanol and citronellal also occurred.

Example 3

A 100 cc autoclave of the same type as used in Example 1-A was charged with 0.1 part of platinum oxide, 30 parts of 90% methanol and 0.075 part of ferrous sulfate heptahydrate. The inside of the autoclave was purged with nitrogen, and then hydrogen was introduced into it to a partial pressure of 10 Kg/cm$^2$.G. The mixture was stirred at room temperature for 1 hour. Then, the stirring was stopped, and the contents of the autoclave were allowed to stand for 30 minutes to sediment platinum oxide. The supernatant liquid was gently taken out, and 0.011 part of zinc acetate dihydrate and 30 parts of 90% methanol were added. The inside of the autoclave was again purged fully with nitrogen and hydrogen, and hydrogen was introduced into it to a partial pressure of 10 Kg/cm$^2$.G. The mixture was stirred at this pressure for 1 hour, and then the stirring was stopped. The contents of the autoclave were allowed to stand for 30 minutes to sediment and separate platinum oxide. This sedimentation procedure was repeated two more times using 20 parts of 90% methanol each time. Analysis of a small amount of the resulting catalyst showed that it had a surface area of 18.5 m$^2$/g, an iron retention of 4.3% by weight, and a zinc retention of 5.5% by weight.

The resulting catalyst, 7.6 parts of citral, and 30 parts of 90% methanol were fed into the autoclave. The inside of the autoclave was purged fully with nitrogen and then with hydrogen. Hydrogen was then introduced to a partial pressure of 30 Kg/cm$^2$.G. The mixture was stirred at this pressure for 4 hours, and then the contents of the autoclave were allowed to stand for 30 minutes to sediment and separate the catalyst. 37 parts of the reaction mixture was obtained. The conversion of citral was 56%, and the selectivity to geraniol was 91.7%. Citronellol also occurred.

EXAMPLE 4

A 100 cc autoclave of the same type as used in Example 3 was charged with 0.1 part of platinum oxide, 30 parts of 90% methanol, and 0.011 part of zinc acetate dihydrate, and the inside of the autoclave was purged fully with nitrogen and then with hydrogen. Then, hydrogen was introduced into the autoclave to a partial pressure of 10 Kg/cm$^2$.G, and the mixture was stirred at this pressure at room temperature for 1 hour. Then, the stirring was stopped, and the contents of the autoclave were allowed to stand to sediment platinum oxide. The supernatant liquid was gently taken out, and 0.075 part of ferrous sulfate heptahydrate and 30 parts of 90% methanol were added. The inside of the autoclave was again fully purged with nitrogen and hydrogen, and then hydrogen was introduced into it to a pressure of 10 Kg/cm$^2$.G. The mixture was stirred for 1 hour at this pressure, and then, the stirring was stopped, after which the contents of the autoclave were allowed to stand for 30 minutes to sediment and separate platinum oxide. This sedimentation procedure was repeated two times more using 20 parts of 90% methanol each time to afford a catalyst. Analysis of a small amount of the catalyst so prepared showed that it had a surface area of 19.4 m$^2$/g, an iron retention of 2.5% by weight and a zinc retention of 5.0% by weight.

The resulting catalyst, 7.6 parts of citral and 30 parts of 90% methanol were fed into the 100 cc autoclave, and the inside of the autoclave was purged fully with nitrogen and then with hydrogen. Then, hydrogen was introduced into the autoclave to a partial pressure of 30 Kg/cm$^2$.G, and at this pressure, the mixture was stirred for 4 hours. Then, the contents of the autoclave were allowed to stand for 30 minutes to sediment and separate the catalyst. The reaction mixture was obtained in an amount of 37 parts. The conversion of citral was 66.2%, and the selectivity to geraniol and nerol was 91.9%. Citronellol also occurred.

COMPARATIVE EXAMPLE 4

The same 500 cc autoclave as used in Example 1-A was charged with 0.5 part of platinum black, 150 parts of 90% methanol, 0.375 part of ferrous sulfate heptahydrate and 0.055 part of zinc acetate dihydrate, and the inside of the autoclave was fully purged with nitrogen and then with hydrogen. Then, hydrogen was introduced into the autoclave to a partial pressure of 10 Kg/cm$^2$.G, and the mixture was stirred at this pressure and at room temperature for 1 hour. Then, the stirring was stopped, and the catalyst was separted by sedimentation. In 35 minutes, a greater part of the platinum black settled. The supernatant liquid which was a little bit blackish was gently taken out, and this sedimentation procedure was repeated two more times using 100 parts of 90% methanol each time to afford a catalyst.

Analysis of a small amount of the catalyst prepared showed that it had a surface area of 30.5 m$^2$/g, an iron retention of 1% by weight and a zinc retention of 3.3% by weight.

The autoclave was charged with the catalyst prepared, 38 parts of citral and 150 parts of 90% methanol, and the inside of the autoclave was fully purged with nitrogen and then with hydrogen. Hydrogen was introduced into the autoclave to a partial pressure of 30 Kg/cm$^2$.G, and the mixture was stirred at this pressure for 4 hours. Then, the contents of the autoclave were allowed to stand for 40 minutes to sediment and separate the catalyst. The reaction mixture was obtained in an amount of 188 parts. The conversion of citral was 7.0%, and the selectivity to geraniol and nerol was 67%. Both the conversion and the selectivity were poor.

COMPARATIVE EXAMPLE 5

A 500 cc autoclave of the same type as used in Example 1-A was charged with 0.5 part of platinum oxide, 150 parts of 90% methanol, 0.0695 part of ferrous sulfate heptahydrate, 0.0658 part of zinc acetate dihydrate, and 38 parts of citral, and the inside of the autoclave was fully purged first with nitrogen and then with hydrogen. Then, hydrogen was introduced into it to a partial pressure of 30 Kg/cm$^2$.G, and the mixture was stirred at this pressure and at room temperature for 4 hours. The stirring was then stopped to separate the catalyst by sedimentation. In 20 minutes, a greater part of the platinum oxide settled. The supernatant liquid which was blackish was gently taken out, and 188 parts of the reaction mixture was separated from the catalyst. Analysis of a small amount of the resulting catalyst showed that it had a surface area of 6.6 m$^2$/g, an iron retention of 1.1% by weight, and a zinc retention of 8.1% by weight. The conversion of citral was 70%, and the selectivity to geraniol and nerol was 79%. As compared with the results obtained in Example 1, the selectivity and the surface area of the catalyst were both low.

COMPARATIVE EXAMPLE 6

A 100 cc autoclave of the same type as used in Example 3 was charged with 0.1 part of platinum oxide, 30 parts of 90% methanol, 0.18 part of ferrous sulfate heptahydrate and 0.04 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 90% methanol each time to afford a catalyst.

Analysis of a small amount of the resulting catalyst showed that it had a surface area of 17.6 m$^2$/g, an iron retention of 3.7% by weight, and a zinc retention of 9.7% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 10.7%, and the selectivity to geraniol and nerol was 60%.

COMPARATIVE EXAMPLE 7

A 100 cc autoclave of the same type as used in Example 3 was charged with 0.1 part of platinum oxide, 30 parts of 90% methanol, 0.018 part of ferrous sulfate heptahydrate and 0.011 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 90% methanol each time to afford a catalyst.

Analysis of a small amount of the resulting catalyst showed that it had a surface area of 13.5 m$^2$/g, an iron retention of 0.6% by weight, and a zinc retention of 5.7% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minures.

The supernatant liquid was gently taken out to afford 37.6 parts of the reaction mixture. The conversion of citral was 31.8%, and the selectivity of geraniol and nerol was 73%.

COMPARATIVE EXAMPLE 8

A 100 cc autoclave of the same type as used in Example 3 was charged with 0.1 part of platinum oxide, 30 parts of 90% methanol, 0.045 part of ferrous sulfate heptahydrate and 0.045 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 90% methanol each time to afford a catalyst.

Analysis of a small amount of the resulting catalyst showed that it had a surface area of 16.2 m$^2$/g, an iron retention of 1.7% by weight, and a zinc retention of 10.6% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 15.0%, and the selectivity to geraniol and nerol was 64.8%.

COMPARATIVE EXAMPLE 9

A 100 cc autoclave of the same type as used in Example 3 was charged with 0.1 part of platinum oxide, 30 parts of 90% methanol and 0.10 part of ferrous sulfate heptahydrate and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 90% methanol each time to afford a catalyst.

Analysis of a small amount of the resulting catalyst showed that it had a surface area of 18.5 m$^2$/g, an iron retention of 4.4% by weight, and a zinc retention of 0% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 76.0%, and the selectivity to geraniol and nerol was 75.5%.

EXAMPLE 5

A 100 cc autoclave of the same type as used in Example 3 was charged with 0.1 part of platinum oxide, 30 parts of 85% methanol, 0.05 parts of ferrous sulfate heptahydrate and 0.01 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 85% methanol each time to afford a catalyst.

Analysis of a small amount of the resulting catalyst showed that it had a surface area of 13.2 m$^2$/g, an iron retention of 1.5% by weight, and a zinc retention of 5.3% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 76.7%, and the selectivity to geraniol and nerol was 93%.

EXAMPLE 6

A 100 cc autoclave of the same type as used in Example 3 was charged with 0.1 part of platinum oxide, 30 parts of methanol, 0.18 part of ferrous sulfate heptahydrate and 0.01 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of methanol each time to afford a catalyst.

Analysis of a small amount of the resulting catalyst showed that it had a surface area of 15.6 m$^2$/g, an iron retention of 43.6% by weight, and a zinc retention of 5.0% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 70.5%, and the selectivity to geraniol and nerol was 91.4%.

EXAMPLE 7

A 100 cc autoclave of the same type as used in Example 3 was charged with 0.1 part of platinum oxide, 30 parts of 80% methanol, 0.1 part of ferrous sulfate heptahydrate and 0.011 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 80% methanol each time to afford a catalyst.

Analysis of a small amount of the resulting catalyst showed that it had a surface area of 37.6 m$^2$/g, an iron retention of 4.6% by weight, and a zinc retention of 5.6% by weight. Then, the resulting catalyst, 7.6 parts of citral and 30 parts of 85% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 84.6%, and the selectivity to geraniol and nerol was 92.8%.

EXAMPLE 8

A 100 cc autoclave of the same type as used in Example 3 was charged with 0.1 part of platinum oxide, 30 parts of 87% methanol, 0.075 part of ferrous sulfate heptahydrate and 0.004 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 87% methanol each time to afford a catalyst.

Analysis of a small amount of the resulting catalyst showed that it had a surface area of 15.7 m$^2$/g, an iron retention of 2.7% by weight, and a zinc retention of 2.3% by weight. Then, the resulting catalyst, 7.6 parts of citral and 30 parts of 90% methanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 77.2%, and the selectivity to geraniol and nerol was 88%.

EXAMPLE 9

A 100 cc autoclave of the same type as used in Example 3 was charged with 0.1 part of platinum oxide, 30 parts of 90% ethanol, 0.12 part of ferrous sulfate heptahydrate and 0.002 part of zinc acetate dihydrate, and the inside of the autoclave was fully purged first with nitrogen and then with hydrogen. Hydrogen was introduced into the autoclave to a partial pressure of 10 Kg/cm$^2$.G, and the mixture was stirred at this pressure and at room temperature for 1 hour. Then, the stirring was stopped to separate platinum oxide by sedimentation. This sedimentation procedure was repeated two more times using 20 parts of 90% ethanol each time to afford a catalyst.

Analysis of a small amount of the resulting catalyst showed that it had a surface area of 14.3 m$^2$g, an iron retention of 12% by weight, and a zinc retention of 0.9% by weight. Then, the resulting catalyst, 7.6 parts of citral and 30 parts of 90% ethanol were fed into the autoclave, and the inside of the autoclave was purged fully with nitrogen and hydrogen. Hydrogen was introduced into the autoclave to a partial pressure of 30 Kg/cm$^2$.G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 80.1%, and the selectivity to geraniol and nerol was 85%.

EXAMPLE 10

A 100 cc autoclave of the same type as used in Example 3 was charged with 0.1 part of platinum oxide, 30 parts of 95% ethanol, 0.12 part of ferrous sulfate heptahydrate and 0.005 part of zinc acetate dihydrate, and the inside of the autoclave was fully purged first with nitrogen and then with hydrogen. Hydrogen was introduced into the autoclave to a partial pressure of 10 Kg/cm$^2$. G, and the mixture was stirred at this pressure and at room temperature for 1 hour. Then, the stirring was stopped to separate platinum oxide by sedimentation. This sedimentation procedure was repeated two more times using 20 parts of 95% ethanol each time to afford a catalyst.

Analysis of a small amount of the resulting catalyst showed that it had a surface area of 15.3 m²/g, an iron retention of 11.8% by weight, and a zinc retention of 2.8% by weight. Then, the resulting catalyst, 7.6 parts of citral and 30 parts of 95% ethanol were fed into the autoclave, and the inside of the autoclave was purged fully with nitrogen and hydrogen. Hydrogen was introduced into the autoclave to a partial pressure of 30 Kg/cm².G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 83.2%, and the selectivity to geraniol and nerol was 96.6%.

EXAMPLE 11

A 100 cc autoclave of the same type as used in Example 3 was charged with 0.1 part of platinum oxide, 30 parts of 95% methanol, 0.12 part of ferrous sulfate heptahydrate and 0.01 part of zinc acetate dihydrate, and the inside of the autoclave was fully purged first with nitrogen and then with hydrogen. Hydrogen was introduced into the autoclave to a partial pressure of 10 Kg/cm².G, and the mixture was stirred at this pressure and at room temperature for 1 hour. Then, the stirring was stopped to separate platinum oxide by sedimentation. This sedimentation procedure was repeated two more times using 20 parts of 95% methanol each time to afford a catalyst.

Analysis of a small amount of the resulting catatlyst showed that it had a surface area of 33 m²/g, an iron retention of 11.6% by weight, and a zinc retention of 4.7% by weight. Then, the resulting catalyst, 7.6 parts of citral and 30 parts of 95% methanol were fed into the autoclave, and the inside of the autoclave was purged fully with nitrogen and hydrogen. Hydrogen was introduced into the autoclave to a partial pressure 30 Kg/cm².G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of citral was 79.0%, and the selectivity to geraniol and nerol was 97%.

EXAMPLE 12

A 100 cc autoclave of the same type as used in Example 3 was charged with 0.1 part of platinum oxide, 30 parts of 90% methanol, 0.075 part of ferrous sulfate heptahydrate and 0.011 part of zinc acetate dihydrate, and the inside of the autoclave was fully purged first with nitrogen and then with hydrogen. Hydrogen was introduced into the autoclave to a partial pressure of 10 Kg/cm².G, and the mixture was stirred at this pressure and at room temperature for 1 hour. Then, the stirring was stopped to separate platinum oxide by sedimentation. This sedimentation procedure was repeated two more times using 20 parts of 90% methanol each time to afford a catalyst.

Analysis of a small amount of the resulting catalyst showed that it had a surface area of 14.7 m²/g, an iron retention of 2.4% by weight, and a zinc retention of 5.6% by weight. Then, the resulting catalyst, 6.6 parts of cinnanyl aldehyde and 30 parts of 90% methanol were fed into the autoclave, and the inside of the autoclave was purged fully with nitrogen and hydrogen. Hydrogen was introduced into the autoclave to a partial pressure of 30 Kg/cm².G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of cinnanyl aldehyde was 88.3%, and the selectivity to cinnanyl alcohol was 100%.

EXAMPLE 13

A 100 cc autoclave of the same type as used in Example 3 was charged with 0.1 part of platinum oxide, 30 parts of 90% methanol, 0.075 part of ferrous sulfate heptahydrate and 0.011 part of zinc acetate dihydrate, and the inside of the autoclave was fully purged first with nitrogen and then with hydrogen. Hydrogen was introduced into the autoclave to a partial pressure of 10 Kg/cm².G, and the mixture was stirred at this pressure and at room temperature for 1 hour. Then, the stirring was stopped to separate platinum oxide by sedimentation. This sedimentation procedure was repeated two more times using 20 parts of 90% methanol each time to afford a catalyst.

Analysis of a small amount of the resulting catalyst showed that it had a surface area of 14.7 m²/g, an iron retention of 2.4% by weight, and a zinc retention of 5.6% by weight. Then, the resulting catalyst, 5.0 parts of trans-2-hexenyl aldehyde and 30 parts of 90% methanol were fed into the autoclave, and the inside of the autoclave was purged fully with nitrogen and hydrogen. Hydrogen was introduced into the autoclave to a partial pressure of 30 Kg/cm².G, and at this pressure, the mixture was stirred for 4 hours. The stirring was stopped, and the inside of the autoclave was purged with nitrogen, after which the contents of the autoclave were allowed to stand for 15 minutes.

The supernatant liquid was gently taken out to afford 37.6 parts of the reaction mixture. The conversion of trans-2-hexenyl aldehyde was 85.0%, and the selectivity to trans-2-hexenyl alcohol was 83.1%.

What we claim is:

1. An improved process for preparing unsaturated alcohols by catalytic hydrogenation of unsaturated aldehydes with hydrogen in the presence of a solid hydrogenating catalyst, said catalyst comprising platinum oxide and deposited on its surface in an atmosphere of hydrogen, an iron compound selected from the group consisting of ferrous sulfate and ferrous acetate and a zinc compound selected from the group consisting of zinc sulfate and zinc acetate, wherein the platinum oxide is reduced by the hydrogen in the presence of the iron and zinc compounds.

2. The process of claim 1 wherein said catalyst has a surface area of 10 to 60 m²/g, and wherein the amounts of the iron compound and the zinc compound present in a skin layer of the solid catalyst which extends from its surface to a depth of 1 micron towards its inside is 1.5 to 70% by weight calculated as iron, and 0.5 to 8% by weight calculated as zinc based on the total amount calculated as metals of the platinum oxide, iron compound and zinc compound present in the skin layer.

3. The process of claim 1 wherein the unsaturated aldehydes are α,β-unsaturated aldehydes of the general formula

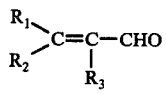

wherein $R_1$ is a saturated or unsaturated hydrocarbon group, and $R_2$ and $R_3$, identical or different to or from each other, represent a hydrogen atom, a saturated or unsaturated hydrocarbon group or a heterocyclic group.

4. The process of claim 1 wherein the catalytic hydrogenation is carried out at a temperature of $-40°$ to $300°$ C.

5. The process of claim 1 wherein the catalytic hydrogenation is carried out repeatedly either batchwise or continuously by recycling the same solid catalyst, and the iron compound and the zinc compound are added to the solid catalyst to be recycled in an amount of 0.0002 to 0.03 part by weight as metallic iron and 0.0002 to 0.004 part by weight as metallic zinc respectively per part by weight of the platinum oxide in the solid catalyst.

* * * * *